(12) United States Patent
Spigelmyer

(10) Patent No.: US 11,723,625 B2
(45) Date of Patent: Aug. 15, 2023

(54) ACOUSTIC LENS OF ENHANCED WEAR RESISTANCE

(71) Applicant: Transducerworks, LLC, Centre Hall, PA (US)

(72) Inventor: Matthew Todd Spigelmyer, Spring Mills, PA (US)

(73) Assignee: TRANSDUCERWORKS, LLC, Centre Hall, PA (US)

(*) Notice: Subject to any disclaimer, the term of this patent is extended or adjusted under 35 U.S.C. 154(b) by 0 days.

(21) Appl. No.: 14/262,164

(22) Filed: Apr. 25, 2014

(65) Prior Publication Data

US 2015/0305714 A1    Oct. 29, 2015

(51) Int. Cl.
| A61B 8/00 | (2006.01) |
| A61D 1/00 | (2006.01) |
| A61B 8/08 | (2006.01) |
| G01S 15/89 | (2006.01) |
| G01S 7/52 | (2006.01) |

(52) U.S. Cl.
CPC ........ A61B 8/4483 (2013.01); G01S 7/52079 (2013.01); G01S 15/8915 (2013.01)

(58) Field of Classification Search
CPC ..... G02F 1/33; A61B 8/4483; G01S 7/52079; G01S 15/8915
USPC ....................................................... 359/305
See application file for complete search history.

(56) References Cited

U.S. PATENT DOCUMENTS

| 4,440,025 A * | 4/1984 | Hayakawa | B06B 1/0633 |
| | | | 310/334 |
| 4,557,146 A * | 12/1985 | Buffington | G10K 11/32 |
| | | | 335/153 |
| 4,699,150 A * | 10/1987 | Kawabuchi | G10K 11/02 |
| | | | 600/446 |
| 5,792,058 A * | 8/1998 | Lee | B06B 1/0622 |
| | | | 600/459 |
| 5,971,925 A * | 10/1999 | Hossack | A61B 8/4281 |
| | | | 600/443 |
| 6,183,578 B1 * | 2/2001 | Ritter | B06B 1/0611 |
| | | | 156/155 |

(Continued)

OTHER PUBLICATIONS

"Class Instrumentation LTD Ultrasonic Sound Velocity Chart" from Class Instrumentation LTD, http://www.classltd.com/sound_velocity_table.html.*

(Continued)

*Primary Examiner* — Joseph M Santos Rodriguez
*Assistant Examiner* — Kaitlyn E Sebastian
(74) *Attorney, Agent, or Firm* — Todd A. Serbin; J. Clint Wimbish; Maynard Nexsen PC

(57) ABSTRACT

In one aspect, ultrasound transducers are described herein comprising acoustic lenses having enhanced wear resistance. Such transducers can be employed in applications having harsh operating conditions, including veterinary applications. A transducer described herein, in some embodiments, comprises a polymeric acoustic lens having an acoustic velocity greater than 1.7 mm/µs, the polymeric acoustic lens arranged over an array of transducer elements wherein the array of transducer elements has a curvature in an elevation plane sufficient to compensate for wave refraction induced by the acoustic velocity of the polymeric acoustic lens to provide elevation focusing of an ultrasound beam generated by the transducer element array.

6 Claims, 5 Drawing Sheets

(56) References Cited

U.S. PATENT DOCUMENTS

| | | | | |
|---|---|---|---|---|
| 6,194,814 B1* | 2/2001 | Hanafy | ................ | G10K 11/006 |
| | | | | 310/327 |
| 6,307,302 B1* | 10/2001 | Toda | ....................... | B06B 1/067 |
| | | | | 310/327 |
| 2002/0007118 A1* | 1/2002 | Adachi | ............... | G01S 15/8922 |
| | | | | 600/443 |
| 2005/0124889 A1* | 6/2005 | Flesch | .................. | A61B 8/4281 |
| | | | | 600/445 |
| 2007/0205698 A1* | 9/2007 | Chaggares | ............ | H01L 41/083 |
| | | | | 310/327 |
| 2008/0156577 A1* | 7/2008 | Dietz | ..................... | G10K 11/30 |
| | | | | 181/176 |
| 2009/0093737 A1* | 4/2009 | Chomas | ................... | A61N 7/02 |
| | | | | 601/2 |
| 2013/0150725 A1* | 6/2013 | Choi | ........................ | A61B 8/08 |
| | | | | 600/472 |
| 2015/0112201 A1* | 4/2015 | Nakanishi | ............ | A61B 8/4494 |
| | | | | 600/472 |
| 2015/0182999 A1* | 7/2015 | Zhao | ..................... | B06B 1/0622 |
| | | | | 310/334 |
| 2015/0183000 A1* | 7/2015 | Tai | ....................... | G01S 7/52017 |
| | | | | 367/7 |
| 2015/0190118 A1* | 7/2015 | Kiyose | ................. | A61B 8/4483 |
| | | | | 600/443 |

OTHER PUBLICATIONS

Basic Physics of Ultrasonographic Imaging, WHO (Year: 2005).*

* cited by examiner

FIGURE 1 – PRIOR ART

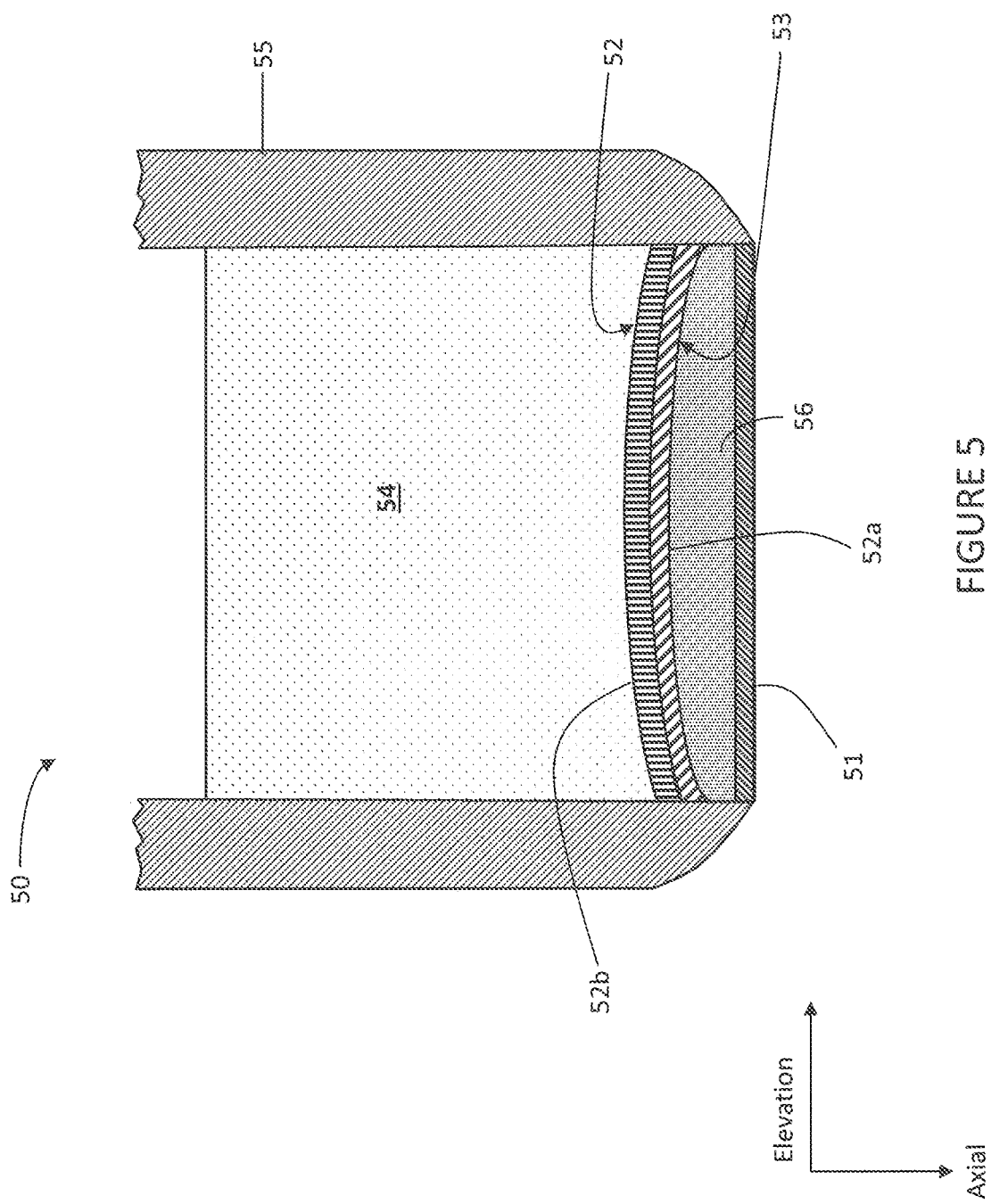

ACOUSTIC LENS OF ENHANCED WEAR RESISTANCE

FIELD

The present invention relates to acoustic lenses and associated ultrasound transducers and, in particular, to acoustic lenses having enhanced wear resistance.

BACKGROUND

A typical approach to ultrasound transducer fabrication often employs a plano/convex room temperature vulcanized (RTV) silicon material lens to provide focus of the ultrasound beam in the elevation plane. Focusing is accomplished due to the difference in acoustic velocity of the RTV material as compared to tissue. This focusing enables a narrow acoustic beam, thereby improving resolution of the transducer. The RTV lens becomes the patient or tissue contact surface and also provides insulation of electrical connections governing operation of the transducer. The acoustic impedance of the RTV material is substantially matched to tissue to minimize reflections at the lens/tissue interface.

In applications, such as veterinary applications, where the transducer is exposed to harsh operating conditions, the RTV lens is quickly worn and becomes a high failure mode. This is especially true for large animal imaging where the transducer is used in the field. Coarse hair, dirt and other environmental factors cause a high degree of abrasion that typical RTV material cannot withstand.

SUMMARY

In one aspect, ultrasound transducers are described herein comprising acoustic lenses having enhanced wear resistance. Such transducers can be employed in applications having harsh operating conditions, including veterinary applications. A transducer described herein, in some embodiments, comprises a polymeric acoustic lens having an acoustic velocity greater than 1.7 mm/µs, the polymeric acoustic lens arranged over an array of transducer elements wherein the array of transducer elements has curvature in an elevation plane sufficient to compensate for wave refraction induced by the acoustic velocity of the polymeric acoustic lens to provide elevation focusing of an ultrasound beam generated by the transducer element array.

In another embodiment, an ultrasound transducer described herein comprises a polymeric acoustic lens arranged over an array of transducer elements, the polymeric acoustic lens having an acoustic velocity greater than 1.7 mm/µs and an exterior surface having curvature in an elevation plane sufficient to compensate for wave refraction induced by the acoustic velocity of the polymeric lens to provide elevation focusing of an ultrasound beam generated by the transducer element array.

In a further embodiment, an ultrasound transducer comprises an array of transducer elements and a polymeric window having an acoustic velocity greater than 1.7 mm/µs arranged over the array of transducer elements. A filler material is positioned between the array of transducer elements and the polymeric window, the array of transducer elements having curvature in an elevation plane sufficient to compensate for wave refraction induced by the acoustic velocity of the polymeric window to provide elevation focusing of an ultrasound beam generated by the transducer element array. Polymeric acoustic lenses and/or polymeric windows of ultrasound transducers described herein, in some embodiments, are formed of a thermoplastic. Further, ultrasound transducers described herein can be linear array, curved array or phased array transducers.

In another aspect, methods of veterinary imaging are described herein. In some embodiments, a method of veterinary imaging comprises providing an ultrasound transducer and imaging tissue of an animal with the ultrasound transducer, the ultrasound transducer comprising a polymeric acoustic lens having an acoustic velocity of greater than 1.7 mm/µs, the polymeric acoustic lens arranged over an array of transducer elements wherein the array of transducer elements has curvature in an elevation plane sufficient to compensate for wave refraction induced by the acoustic velocity of the polymeric acoustic lens to provide elevation focusing of an ultrasound beam generated by the transducer element array.

In another embodiment, a method of veterinary imaging comprises providing an ultrasound transducer and imaging tissue of an animal with the ultrasound transducer, the ultrasound transducer comprising a polymeric acoustic lens arranged over an array of transducer elements, the polymeric acoustic lens having an acoustic velocity greater than 1.7 mm/µs and an exterior surface having curvature in an elevation plane sufficient to compensate for wave refraction induced by the acoustic velocity of the polymeric lens to provide elevation focusing of an ultrasound beam generated by the transducer element array.

In a further embodiment, a method of veterinary imaging comprises providing an ultrasound transducer and imaging tissue of an animal with the ultrasound transducer, the ultrasound transducer comprising an array of transducer elements and a polymeric window having an acoustic velocity greater than 1.7 mm/µs arranged over the array of transducer elements. A filler material is positioned between the array of transducer elements and the polymeric window, the array of transducer elements having curvature in an elevation plane sufficient to compensate for wave refraction induced by the acoustic velocity of the polymeric window to provide elevation focusing of an ultrasound beam generated by the transducer element array.

In embodiments of methods described herein, the polymeric acoustic lens and polymeric window display resistance to wear by environmental factors including animal hair and/or dirt, thereby enhancing the lifetime of the ultrasound tranducer.

These and other embodiments are described in further detail in the detailed description which follows.

BRIEF DESCRIPTION OF THE DRAWINGS

FIG. 5 illustrates a cross-sectional view along an elevation plane of an ultrasound transducer according to one embodiment described herein.

DETAILED DESCRIPTION

Embodiments described herein can be understood more readily by reference to the following detailed description, examples and drawings and their previous and following descriptions. Elements, apparatus and methods described herein, however, are not limited to the specific embodiments presented in the detailed description, examples and drawings. It should be recognized that these embodiments are merely illustrative of the principles of the present invention. Numerous modifications and adaptations will be readily apparent to those of skill in the art without departing from the spirit and scope of the invention.

I. Ultrasound Transducers

Figure 1:
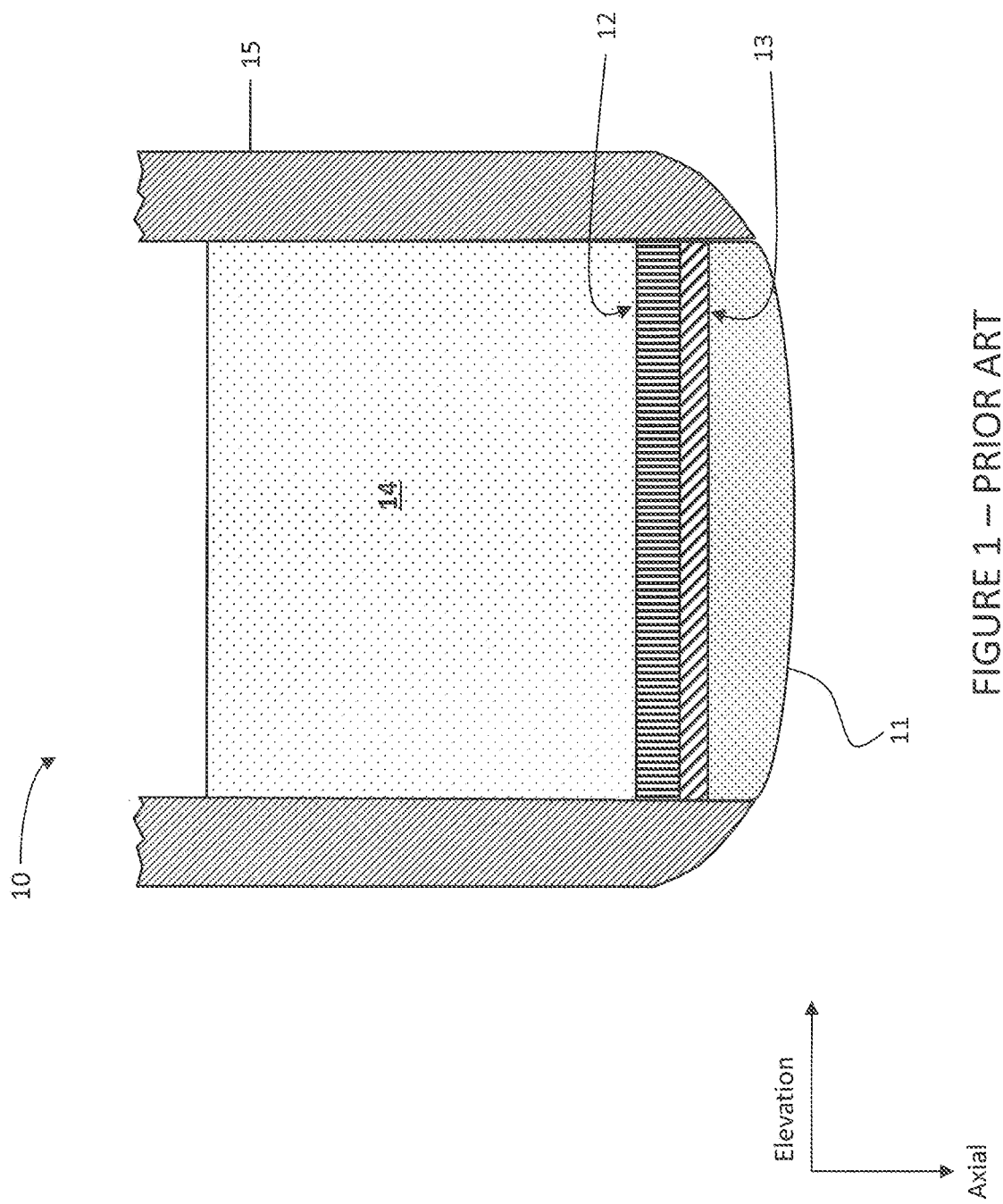
FIG. 1 illustrates a cross-sectional view along an elevation plane of a prior ultrasound transducer.

FIG. 1 illustrates a cross-sectional view along an elevation plane of a prior ultrasound transducer having a typical structure. The ultrasound transducer (10), for example, employs a lens (11) formed of a RTV material and positioned over a planar transducer element array (12). One or more matching layers (13) are positioned between the RTV lens (11) and the planar transducer element array (12). Further, the transducer element array (12) is coupled to a backing (14), wherein the backing (14), transducer element array (12), matching layer(s) (13) and portion of the RTV lens (11) are housed in a casing (15). The plano/convex RTV lens (11) provides focusing of the ultrasound beam in the elevation plane and serves as the tissue contact point for the ultrasound transducer (10). In being the outermost contact surface, the RTV lens (11) does not demonstrate desirable wear characteristics rendering the ultrasound transducer unsuitable for field use or deployment in other harsh environments. Wear-resistant impedance matched thermoplastics can replace or be positioned over the RTV lens. Such materials, however, have higher acoustic velocities disrupting elevation focus capabilities.

However, ultrasound transducers are described herein comprising acoustic lenses having enhanced wear resistance while maintaining elevation focusing. Such transducers can be used in applications having harsh operating conditions, including veterinary applications without loss of spectral resolution. A transducer described herein, in some embodiments, comprises a polymeric acoustic lens having an acoustic velocity greater than 1.7 mm/µs, the polymeric acoustic lens arranged over an array of transducer elements wherein the array of transducer elements has curvature in an elevation plane sufficient to compensate for wave refraction induced by the acoustic velocity of the polymeric acoustic lens to provide elevation focusing of an ultrasound beam generated by the transducer element array.

Figure 2:
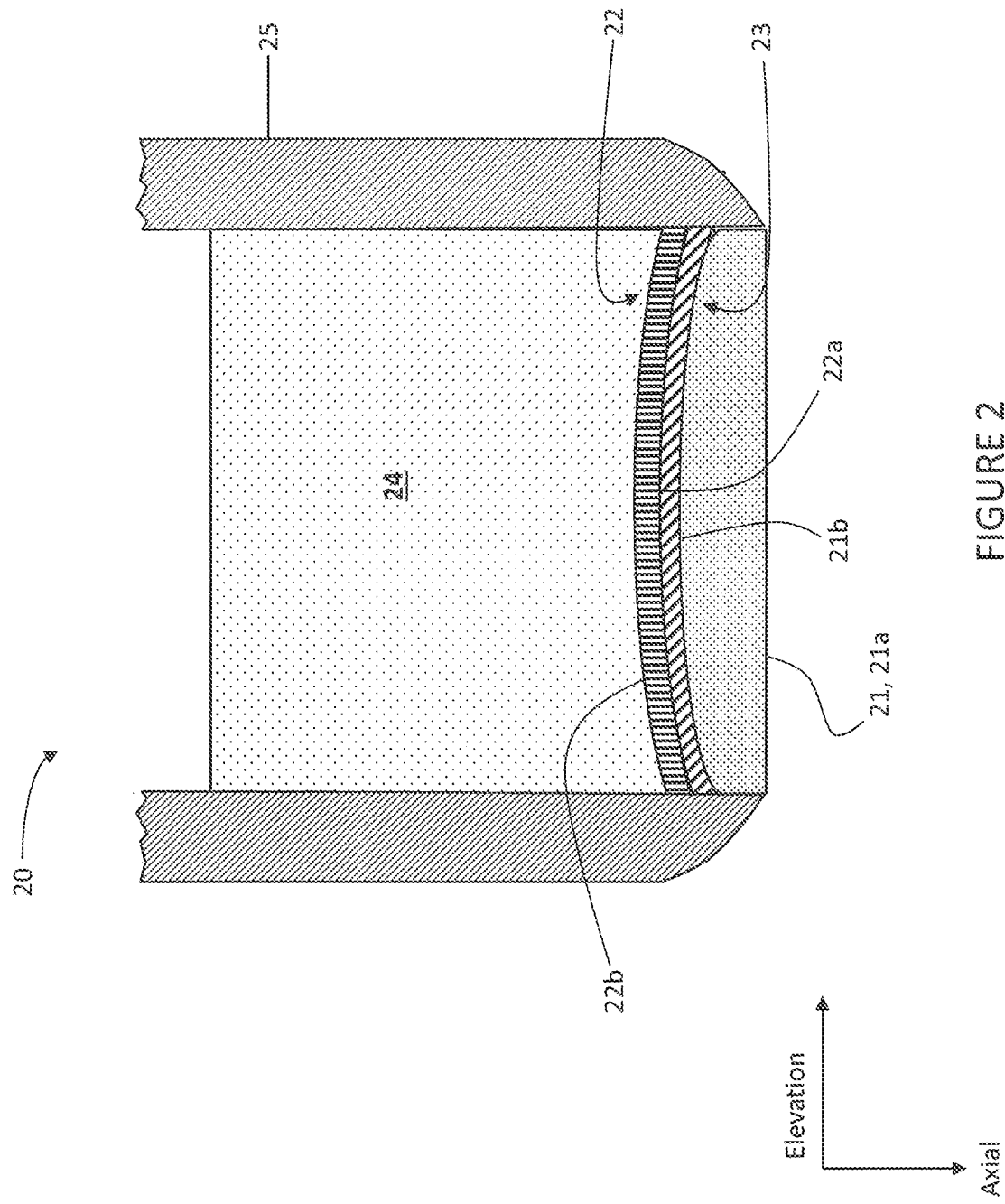
FIG. 2 illustrates a cross-sectional view along an elevation plane of an ultrasound transducer according to one embodiment described herein.

FIG. 2 illustrates a cross-sectional view along an elevation plane of an ultrasound transducer according to one embodiment described herein. The ultrasound transducer (20) of FIG. 2 comprises a polymeric acoustic lens (21) positioned over an array of transducer elements (22) having curvature in the elevation plane. The curvature of the transducer element array (22) is sufficient to compensate for wave refraction induced by the higher acoustic velocity of the polymeric acoustic lens (21) to provide elevation focusing of an ultrasound beam generated by the transducer element array (22). Therefore, resolution of the ultrasound transducer (20) is maintained while enhancing durability and wear-resistance of the acoustic lens (21).

In the embodiment of FIG. 2, a first surface (22a) of the transducer element array (22) facing the material of examination is concave in the elevation plane. Similarly, the second surface (22b) in facing opposition to the first surface (22a) is concave in the elevation plane. In such embodiments, transducer elements of the array (22) can have substantially uniform thickness. Alternatively, the second surface (22b) can be planar or substantially planar. When the second surface (22b) is planar or substantially planar, trans- ducer elements of the array (22) can display varying thickness in the elevation direction to provide the concave first surface (22a). Transducer elements of the array (22) can have any construction not inconsistent with the objectives of the present invention. In some embodiments, transducer elements are formed of a piezoelectric material. Suitable piezoelectric materials can be a monolithic ceramic or a composite material, such as a ceramic-epoxy composite.

One or more matching layers (23) are positioned between the polymeric acoustic lens (21) and transducer element array (22). The one or more matching layers (23) have a curvature substantially matching that of the transducer element array (22). In some embodiments, for example, a first layer of acoustic matching material with high impedance is cast onto the transducer element array (22), and a second layer of acoustic matching material of low impedance is cast onto the first matching layer. In the embodiment of FIG. 2, filler material does not reside between the polymeric acoustic lens (21) and the matching layer(s) (23). The polymeric acoustic lens (21) directly contacts the matching layer(s) (23). In some embodiments, impedance matched adhesive, such as a polyurethane can be used to bond the acoustic lens (21) to the outermost matching layer (23). In being in direct contact with a matching layer (23), the interior surface (21b) of the polymeric acoustic lens (21) has a curvature substantially matching the curvature of the transducer element array (22). The exterior surface (21a) of the polymeric acoustic lens (21) is planar or substantially planar.

As described herein, the polymeric acoustic lens has an acoustic velocity greater than 1.7 mm/µs. In some embodiments, the polymeric acoustic lens has an acoustic velocity selected from Table I.

TABLE I

| Acoustic Velocity of Polymeric Acoustic Lens (mm/µs) |
| --- |
| 1.75-2.2 |
| 1.8-2.0 |
| 1.8-2.2 |
| 1.9-2.2 |
| 2.0-2.2 |

Curvature of the transducer element array can be determined according to the acoustic velocity of the polymeric lens. Therefore, polymeric acoustic lenses formed of materials having differing acoustic velocities will necessitate different curvatures of the transducer element array to compensate for soundwave refraction and provide elevation focusing of the ultrasound beam.

Further, the polymeric acoustic lens can have an acoustic impedance of 1.5 MRayls to 1.9 MRayls. In some embodiments, for example, the polymeric acoustic lens is formed of thermoplastic. Specifically, the polymeric acoustic lens can be formed of polymer selected from the group consisting of polyethylene, polymethylpentene (TPX) and ionomer such as SURLYN®.

Referring once again to FIG. 2, the transducer element array (22) is coupled to a backing material (24), wherein the backing (24), transducer element array (22), matching layer(s) (23) and portion of the polymeric acoustic lens (21) are housed in a casing (25).

Figure 3:
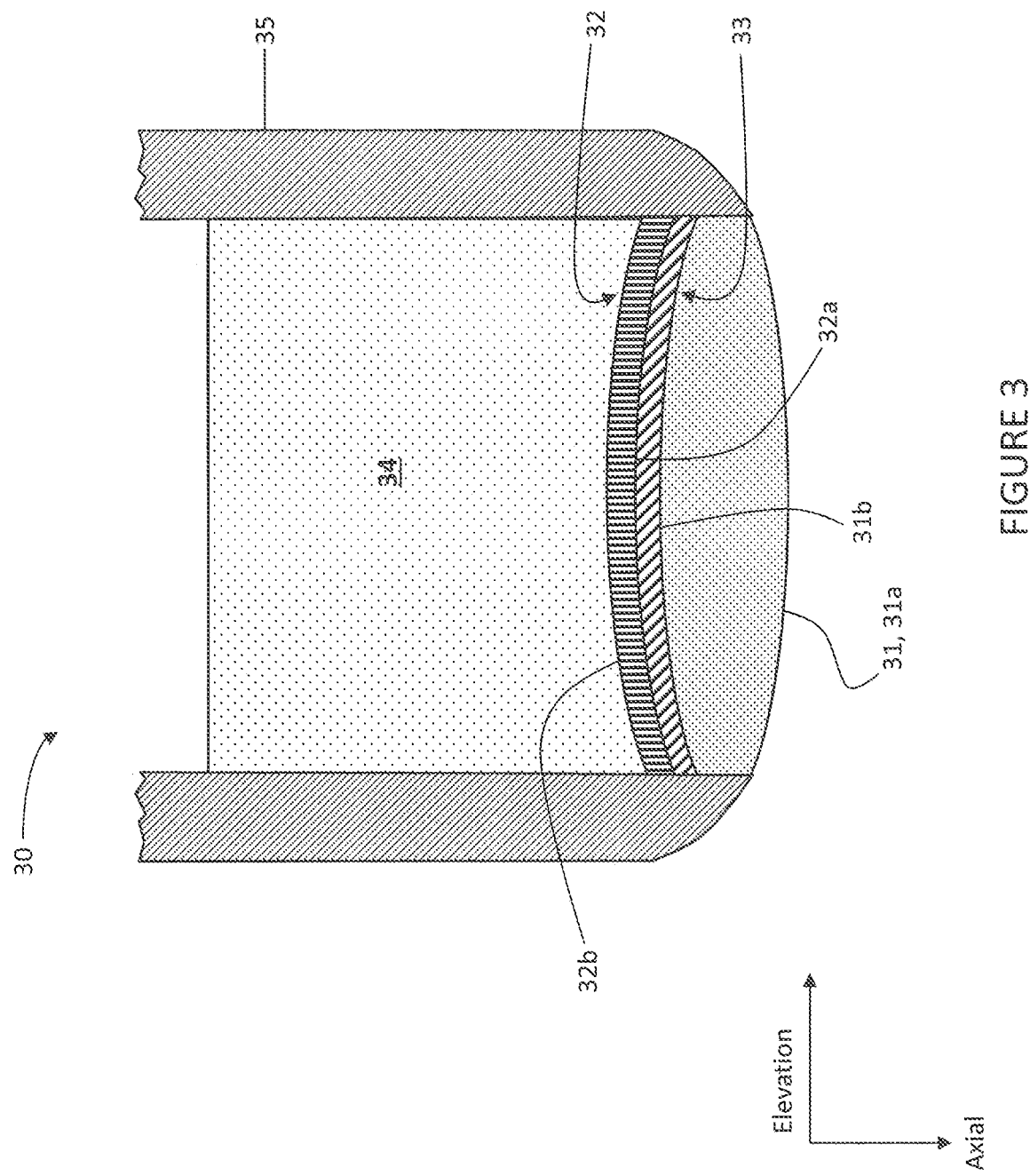
FIG. 3 illustrates a cross-sectional view along an elevation plane of an ultrasound transducer according to one embodiment described herein.

FIG. 3 illustrates a cross-sectional view along an elevation plane of an ultrasound transducer according to another embodiment described herein. The ultrasound transducer (30) of FIG. 3 is similar in construction to the transducer of FIG. 2. The polymeric acoustic lens (31) is positioned over the transducer element array (32), the transducer element array (32) having curvature in the elevation plane. In the embodiment of FIG. 3, a first surface (32a) of the transducer element array (32) facing the material of examination is concave in the elevation plane. Similarly, the second surface (32b) in facing opposition to the first surface (32a) is concave in the elevation plane. In such embodiments, the transducer elements of the array (32) can have substantially uniform thickness. Alternatively, the second surface (32b) can be planar or substantially planar. When the second surface (32b) is planar or substantially planar, transducer elements of the array (32) can display varying thickness in the elevation direction to provide the concave first surface (32a).

One or more matching layers (33) are positioned between the polymeric acoustic lens (31) and transducer element array (32). The one or more matching layers (33) have a curvature substantially matching that of the transducer element array (32). In some embodiments, for example, a first layer of acoustic matching material with high impedance is cast onto the transducer element array (32), and a second layer of acoustic matching material of low impedance is cast onto the first matching layer. Further, filler material does not reside between the polymeric acoustic lens (31) and the matching layer(s) (33). The polymeric acoustic lens (31) directly contacts the outermost matching layer (33). An impedance matched adhesive, such as a polyurethane can be used to bond the acoustic lens (31) to the outermost matching layer (33). In being in direct contact with a matching layer (33), the interior surface (31b) of the polymeric acoustic lens (31) has a curvature substantially matching the curvature of the transducer element array (32). The exterior surface (31a) of the polymeric acoustic lens (31) is convex to facilitate patient contact.

Figure 4:
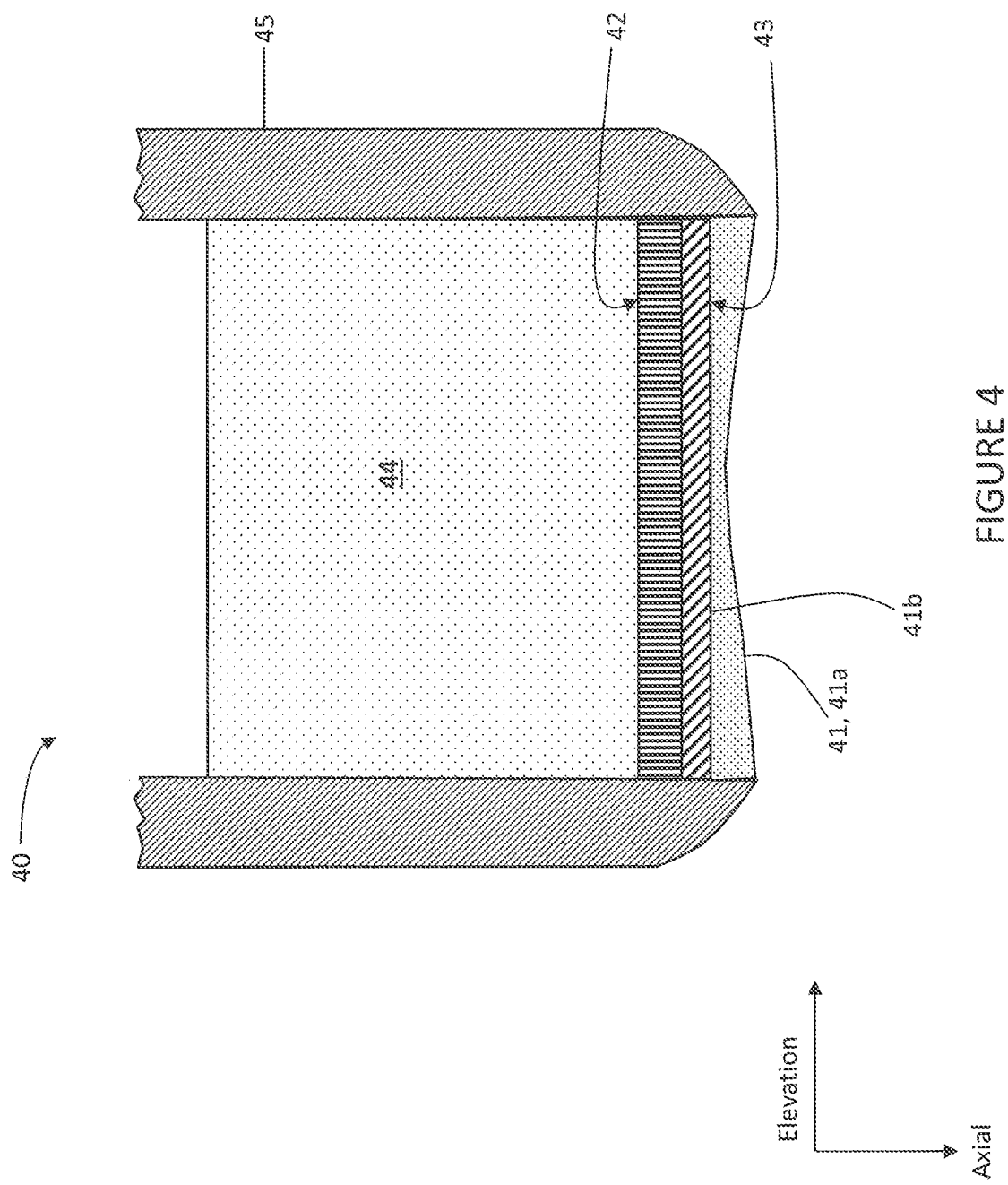
FIG. 4 illustrates a cross-sectional view along an elevation plane of an ultrasound transducer according to one embodiment described herein.

In another aspect, an ultrasound transducer described herein comprises a polymeric acoustic lens arranged over an array of transducer elements, the polymeric acoustic lens having an acoustic velocity greater than 1.7 mm/μs and an exterior surface having curvature in an elevation plane sufficient to compensate for wave refraction induced by the acoustic velocity of the polymeric lens to provide elevation focusing of an ultrasound beam generated by the transducer element array. FIG. 4 illustrates an ultrasound transducer having this construction.

As illustrated in FIG. 4, the ultrasound transducer (40) comprises a polymeric acoustic lens (41) arranged over a transducer element array (42). Unlike the embodiments of FIGS. 2 and 3, the transducer element array (42) is not curved and is planar or substantially planar in the elevation plane. The polymeric acoustic lens (41) includes an exterior surface (41a) having a curvature in an elevation plane sufficient to compensate for wave refraction induced by the acoustic velocity of the polymeric lens to provide elevation focusing of an ultrasound beam generated by the transducer element array. The interior surface (41b) of the polymeric acoustic lens (41) is planar or substantially planar consistent with the planar matching layer (43) to which the acoustic lens (41) is coupled. As described herein, the polymeric acoustic lens (41) can be in direct contact with the matching layer (43). In some embodiments, the polymeric acoustic lens (41) is bonded to the matching layer (43) by an adhesive, such as a urethane adhesive.

The polymeric acoustic lens (41) can be formed of any polymeric material described herein and can have an acoustic velocity selected from Table I. Further, the acoustic lens (41) can have an acoustic impedance of 1.5 MRayls to 1.9 MRayls. Curvature of the exterior surface of the polymeric acoustic lens (41) can be determined according to the acoustic velocity of the lens (41). Therefore, polymeric acoustic lenses formed of materials having differing acoustic velocities will necessitate different curvatures of the exterior surface to compensate for wave refraction and provide elevation focusing of the ultrasound beam. Further, the transducer element array (42) of FIG. 4 is coupled to a backing material (44), wherein the backing (44), transducer element array (42), matching layer(s) (43) and portion of the polymeric acoustic lens (41) are housed in a casing (45).

In a further aspect, an ultrasound transducer comprises an array of transducer elements and a polymeric window having an acoustic velocity greater than 1.7 mm/μs arranged over the array of transducer elements. A filler material is positioned between the array of transducer elements and polymeric window, the array of transducer elements having curvature in an elevation plane sufficient to compensate for wave refraction induced by the acoustic velocity of the polymeric window to provide elevation focusing of an ultrasound beam generated by the transducer element array. FIG. 5 illustrates an ultrasound transducer having this construction.

As illustrated in FIG. 5, the ultrasound transducer (50) comprises a polymeric window (51) arranged over a transducer element array (52). The polymeric window (51) can be formed of any polymeric material described herein and can have an acoustic velocity selected from Table I. Further, the polymeric window can have an acoustic impedance of 1.5 MRayls to 1.9 MRayls.

Additionally, the polymeric window (51) is substantially planar and is of uniform or substantially uniform thickness. The transducer element array (52) has curvature in the elevation plane. In the embodiment of FIG. 5, a first surface (52a) of the transducer element array (52) facing the material of examination is concave in the elevation plane. Similarly, the second surface (52b) in facing opposition to the first surface (52a) is concave in the elevation plane. In such embodiments, transducer elements of the array (52) can have substantially uniform thickness. Alternatively, the second surface (52b) can be planar or substantially planar. When the second surface (52b) is planar or substantially planar, transducer elements of the array (52) can display varying thickness to provide the concave first surface (52a).

One or more matching layers (53) are positioned between the polymeric window (51) and transducer element array (52). The one or more matching layers (53) have curvature substantially matching that of the transducer element array (52). In some embodiments, for example, a first layer of acoustic matching material with high impedance is cast onto the transducer element array (52), and a second layer of acoustic matching material of low impedance is cast onto the first matching layer. Further, filler material (56) is positioned between the outermost matching layer (53) and polymeric window (51). Any suitable filler material not inconsistent with the objectives of the present invention can be used. In some embodiments, for example, the filler material is a non-focusing material such as a urethane or RTV. Alternatively, the filler material may be slightly focusing. The transducer element array (52) is coupled to a backing material (54), wherein the backing (54), transducer element array (52), matching layer(s) (53), filler material (56) and portion of the polymeric window (51) are housed in a casing (55).

As described herein, curvature of the transducer element array can be determined according to the acoustic velocity of the polymeric window. Therefore, polymeric acoustic windows formed of materials having differing acoustic velocities will necessitate different curvatures of the transducer element array to compensate for wave refraction and provide elevation focusing of the ultrasound beam.

II. Methods of Veterinary Imaging

In another aspect, methods of veterinary imaging are described herein. In some embodiments, a method of veterinary imaging comprises providing an ultrasound transducer and imaging tissue of an animal with the ultrasound transducer, the ultrasound transducer comprising a polymeric acoustic lens having an acoustic velocity of greater than 1.7 mm/µs, the polymeric acoustic lens arranged over an array of transducer elements wherein the array of transducer elements has curvature in an elevation plane sufficient to compensate for wave refraction induced by the acoustic velocity of the polymeric acoustic lens to provide elevation focusing of an ultrasound beam generated by the transducer element array.

In another embodiment, a method of veterinary imaging comprises providing an ultrasound transducer and imaging tissue of an animal with the ultrasound transducer, the ultrasound transducer comprising a polymeric acoustic lens arranged over an array of transducer elements, the polymeric acoustic lens having an acoustic velocity greater than 1.7 mm/µs and an exterior surface having curvature in an elevation plane sufficient to compensate for wave refraction induced by the acoustic velocity of the polymeric lens to provide elevation focusing of an ultrasound beam generated by the transducer element array.

In a further embodiment, a method of veterinary imaging comprises providing an ultrasound transducer and imaging tissue of an animal with the ultrasound transducer, the ultrasound transducer comprising an array of transducer elements and a polymeric window having an acoustic velocity greater than 1.7 mm/µs arranged over the array of transducer elements. A filler material is positioned between the array of transducer elements and the polymeric window, the array of transducer elements having curvature in an elevation plane sufficient to compensate for wave refraction induced by the acoustic velocity of the polymeric window to provide elevation focusing of an ultrasound beam generated by the transducer element array.

Ultrasound transducers of methods described herein can have any construction and/or properties described in Section I above. Additionally, in embodiments of methods described herein, the polymeric acoustic lens and/or polymeric window display resistance to wear by environmental factors including animal hair and/or dirt, thereby enhancing the lifetime of the ultrasound transducer.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method comprising:
   determining the curvature of an exterior surface of an ultrasound transducer having a polymeric acoustic lens formed of thermoplastic, has a planar interior surface, wherein the exterior surface is configured with a concave curvature in the elevation plane that compensates for wave refraction induced by the acoustic velocity of the polymeric acoustic lens, provides elevation focusing of an ultrasound beam generated by the transducer element array and is uncovered; and,
   providing the ultrasound transducer and imaging tissue of an animal with the ultrasound transducer, wherein the ultrasound transducer further comprises,
   the polymeric acoustic lens having an acoustic velocity of greater than 1.7 mm/µs, the polymeric acoustic lens arranged over an array of transducer elements that have a uniform axial thickness along the elevation plane, wherein the array of transducer elements is planar in an elevation plane;
   at least one matching layer positioned between the polymeric acoustic lens and the array of transducer elements; and
   a casing covering side edges of the concave polymeric acoustic lens completely.

2. The method of claim 1, further comprising designing the polymeric acoustic lens with an acoustic velocity ranging from 1.75 mm/µs to 2.2 mm/µs.

3. The method of claim 1, further comprising designing the polymeric acoustic lens with an acoustic impedance of 1.5 MRayls to 1.9 MRayls.

4. The method of claim 1, further comprising placing the polymeric acoustic lens in direct contact with the at least one matching layer.

5. The method of claim 1, further comprising positioning a filler material between the polymeric acoustic lens and the array of transducer elements.

6. The method of claim 1, further comprising forming the polymeric acoustic lens of a polymer selected from the group consisting of polyethylene, polymethylpentene and ionomer.

* * * * *